(12) United States Patent
Brereton et al.

(10) Patent No.: US 9,333,304 B2
(45) Date of Patent: May 10, 2016

(54) NEEDLE SAFETY ARRANGEMENT AND METHOD FOR OPERATING IT

(75) Inventors: Simon Francis Brereton, Cambridge (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 564 days.

(21) Appl. No.: 13/806,323

(22) PCT Filed: Jun. 27, 2011

(86) PCT No.: PCT/EP2011/060728
§ 371 (c)(1),
(2), (4) Date: Jun. 27, 2013

(87) PCT Pub. No.: WO2012/000940
PCT Pub. Date: Jan. 5, 2012

(65) Prior Publication Data
US 2013/0274666 A1    Oct. 17, 2013

(30) Foreign Application Priority Data
Jun. 28, 2010   (EP) .................................... 10167502

(51) Int. Cl.
*A61M 5/32* (2006.01)
*A61M 5/20* (2006.01)
*A61M 5/46* (2006.01)

(52) U.S. Cl.
CPC ............ *A61M 5/3202* (2013.01); *A61M 5/2033* (2013.01); *A61M 5/46* (2013.01); *A61M 5/326* (2013.01); *A61M 2005/206* (2013.01); *A61M 2005/208* (2013.01); *A61M 2005/3247* (2013.01)

(58) Field of Classification Search
CPC ............ A61M 5/2033; A61M 5/3202; A61M 5/3257; A61M 5/46; A61M 2005/206; A61M 2005/2013
USPC ................... 604/117, 135, 157, 198
See application file for complete search history.

(56) References Cited

U.S. PATENT DOCUMENTS 5,425,715 A  *  6/1995  Dalling et al. ................. 604/136
5,496,286 A  *  3/1996  Stiehl ....................... A61M 5/24
                                                                604/232

(Continued)

FOREIGN PATENT DOCUMENTS

WO         01/45776         6/2001
WO         2007/066152      6/2007
WO         2008/110322      9/2008

OTHER PUBLICATIONS

International Search Report for Int. App. No. PCT/EP2011/060728, completed Apr. 5, 2012.

*Primary Examiner* — Gerald Landry, II
(74) *Attorney, Agent, or Firm* — Fish & Richardson P.C.

(57) ABSTRACT

The invention refers to an auto-injector for administering a dose of a liquid medicament (M), the auto-injector having a distal end (P) and a proximal end (D) with an orifice intended to be applied against an injection site and comprising:
an elongate housing arranged to contain a syringe with a hollow needle and a stopper for sealing the syringe and displacing the medicament (M), wherein the syringe (3) is slidably arranged with respect to the housing,
a drive means capable of, upon activation:
pushing the needle from a retracted position into an advanced position through the orifice and past the proximal end (P), and
operating the syringe to supply the dose of medicament (M),
a plunger for transmitting power from the drive means to the syringe and/or stopper,
activating means arranged to lock the drive means in a compressed state prior to manual operation and capable of, upon manual operation, releasing the drive means for injection,
characterized in that translation of the needle and the syringe and/or translation of the plunger in longitudinal direction is controlled by at least one ramp or one thread so as to cause the syringe and/or the plunger to rotate when translated at least during part of the translation.

15 Claims, 7 Drawing Sheets

(56) References Cited

U.S. PATENT DOCUMENTS

| | | | |
|---|---|---|---|
| 5,637,094 A * | 6/1997 | Stewart et al. | 604/135 |
| 6,939,319 B1 * | 9/2005 | Anstead | A61M 5/30 604/68 |
| 2002/0095120 A1 | 7/2002 | Larsen et al. | |
| 2003/0069543 A1 * | 4/2003 | Carpenter | A61M 25/0084 604/190 |
| 2003/0105430 A1 * | 6/2003 | Lavi et al. | 604/136 |
| 2005/0027255 A1 * | 2/2005 | Lavi | A61M 5/2033 604/135 |
| 2005/0209553 A1 * | 9/2005 | Landau | A61M 5/30 604/72 |
| 2006/0167413 A1 * | 7/2006 | Marshall et al. | 604/110 |
| 2007/0265568 A1 * | 11/2007 | Tsals et al. | 604/136 |
| 2010/0010454 A1 * | 1/2010 | Marshall et al. | 604/208 |
| 2010/0036320 A1 * | 2/2010 | Cox et al. | 604/135 |
| 2012/0172793 A1 * | 7/2012 | Cronenberg | A61J 1/2096 604/87 |

* cited by examiner

NEEDLE SAFETY ARRANGEMENT AND METHOD FOR OPERATING IT

CROSS REFERENCE TO RELATED APPLICATIONS

The present application is a U.S. National Phase Application pursuant to 35 U.S.C. §371 of International Application No. PCT/EP2011/060728 filed Jun. 26, 2011, which claims priority to European Patent Application No. 10167502.3 filed Jun. 28, 2010. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger then the injection will also stop. This means that the user can deliver an under-dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The terms "clockwise" and "counter-clockwise" in the context of this specification refer to senses of rotation with the auto-injector pointing with its distal end towards the observer.

According to the invention an auto-injector is provided for administering a dose of a liquid medicament. The auto-injector has a distal end and a proximal end with an orifice intended to be applied against an injection site. Furthermore, the auto-injector comprises:

an elongate housing arranged to contain a syringe with a hollow needle and a stopper for sealing the syringe and displacing the medicament, wherein the syringe is slidably arranged with respect to the housing,    a drive means capable of, upon activation:

pushing the needle from a retracted position into an advanced position through the orifice and past the proximal end, and       operating the syringe to supply the dose of medicament,    a plunger for transmitting power from the drive means to the syringe and/or stopper,    activating means arranged to lock the drive means in a compressed state prior to manual operation and capable of, upon manual operation, releasing the drive means for injection.

Translation of the needle and the syringe and/or translation of the plunger in longitudinal direction is controlled by at least one ramp or one thread so as to cause the syringe and/or the plunger to rotate when translated at least during part of the translation. Hence, a different dimension, i.e. the circumferential dimension is used for controlling the syringe and needle translation. This means that no additional radial space is taken up by latch clearances and movement, as would be needed with linear control latches in conventional art auto-injectors. Therefore the overall diameter of the auto-injector may be minimised without sacrificing latch strength or stiffness. However, additional linear latches may be used for including more functionality.

The auto-injector according to the invention has a particularly low part count compared to most conventional auto-injectors.

The plunger is preferably arranged to be rotated by at least one ramp or thread on translation from an initial distal position in proximal direction. The activating means comprises a trigger button arranged to be engaged with the plunger so as to prevent rotation and thus translation of the plunger prior to manual operation. The trigger button is arranged to be disengaged from the plunger when being manually operated so as to no longer restrict rotation.

A needle sheath having essentially the shape of a hollow cylinder may be arranged to surround the needle. The needle sheath is slidable in longitudinal direction with respect to the syringe and biased in proximal direction. In the initial state the needle sheath is in its initial position protruding beyond a proximal end of the housing. The needle sheath may be arranged to directly or indirectly engage the plunger in a manner to prevent rotation and thus translation of the plunger in the initial state. The plunger is disengaged from the needle sheath upon translation of the needle sheath in distal direction from the initial position so as to no longer restrict rotation.

The plunger may be engaged directly by a part of the needle sheath or indirectly by a component permanently or temporarily coupled to the needle sheath. Preferably, both, the trigger button and the needle sheath are arranged to engage the plunger. Starting an injection thus requires two actions: pressing the needle sheath against the injection site and operating the trigger button. This reduces the risk for inadvertently triggering the auto-injector.

Due to the ramp the plunger can neither translate when prevented from rotating nor rotate when not translated. Therefore the plunger cannot translate for inserting the needle unless being disengaged from the needle sheath or the trigger button or both.

As an example of a component temporarily coupled to the needle sheath a sheath linkage with at least one linkage leg, slidable in longitudinal direction may be provided. Furthermore a syringe carrier for holding the syringe may be arranged. The syringe and syringe carrier are arranged for joint axial translation and rotation relative to the needle sheath.

The sheath linkage comprises means for restricting translation in proximal direction with respect to the syringe. The means may be a collar or a shoulder abutting distally against the syringe carrier. In an initial state the sheath linkage is abutted against the syringe carrier and latched to the needle sheath for joint axial translation. The syringe carrier exhibits at least one cam on its circumference. The cam is arranged to de-latch the needle sheath from the sheath linkage on rotation of the syringe carrier so as to release the needle sheath for being translated in proximal direction and cover the needle. In an injection cycle the syringe and syringe carrier have to be translated in proximal direction so as to insert the needle into an injection site, e.g. a patient's skin. The rotation of the syringe carrier required for de-latching the needle sheath from the sheath linkage may occur during this translation.

A distal wide end of the linkage leg may be arranged to engage the plunger in a manner to prevent rotation and thus translation of the plunger in the initial state. In the initial state the needle sheath is in its initial position protruding beyond a proximal end of the housing. The wide end is furthermore arranged to disengage from the plunger on translation of the needle sheath and sheath linkage in distal direction from the initial position. Thus, in order to start an injection cycle, the needle sheath has to be pressed against the injection site. Consequently, the needle sheath and the sheath linkage translate in distal direction thereby disengaging the plunger from the distal wide end of the linkage arm and allowing them to rotate.

The syringe carrier may exhibit at least one slot on its circumference. The latched needle sheath and sheath linkage may form at least one spline, each spline arranged for engaging one of the slots in the initial position so as to prevent rotation of the syringe carrier. The spline may be arranged to be disengaged from the slot on translation of the needle sheath in distal direction from the initial position. This avoids premature release of the needle sheath. Instead, the needle sheath has first to be translated in distal direction, e.g. by being pressed against the injection site.

The syringe carrier may be arranged to be rotated by at least one ramp on translation from an initial distal position in proximal direction so as to de-latch the needle sheath from the sheath linkage. The ramp may be arranged on the syringe carrier and/or on a housing or main body in which the syringe carrier rotates. Due to the ramp the syringe carrier can neither translate when prevented from rotating nor rotate when not translated. The syringe carrier, the syringe and the needle can therefore not translate for inserting the needle unless the needle sheath is pushed from its initial position in distal direction since the spline otherwise prevents rotation of the syringe carrier.

The needle sheath may comprise at least one sheath leg extending from the needle sheath in distal direction. The spline consists of a distal end portion of the sheath leg and a proximal end portion of the linkage leg. A rib may protrude inwards from the distal end of the sheath leg. The rib has an aperture for accommodating the proximal end of the linkage leg. The proximal end portion of the linkage leg comprises an inwardly biased resilient tongue connected to the linkage leg at one end and with the other free end engaged proximally behind the rib in the initial position so as to prevent removal of the proximal end portion of the linkage leg through the aperture in the rib. The sheath linkage and the needle sheath are thus latched together. The tongue is arranged to be flexed outwards by the cam on rotation of the syringe carrier so as to align it with the linkage leg and allow the linkage leg to be at least partially pulled out of the aperture in the rib thus de-latching the needle sheath and the sheath linkage. Preferably, at least two or three linkage legs and sheath legs may be provided.

In a preferred embodiment the drive means is a compression spring distally grounded in the housing and proximally pushing on the plunger. The plunger is arranged to be rotated by at least one ramp on translation from an initial distal position in proximal direction similarly to the rotation of the syringe holder.

The angles and widths of the ramps for rotating the syringe carrier and the plunger are preferably matched so as to rotate the plunger, the syringe and the syringe carrier as a single body.

In a preferred embodiment rotation of the syringe by the ramps stops before the needle protrudes from the proximal end of the housing or from the needle sheath. The subsequent motion of the syringe and needle is purely linear so the needle does not screw into the injection site.

In an alternative embodiment the auto-injector may be arranged to rotate the plunger, the syringe carrier, the syringe and the needle until reaching the injection depth even during needle insertion.

At least one resilient latch may be arranged on the circumference of the syringe carrier for flexing outwards into a respective recess in the housing when the syringe carrier, syringe and needle have been translated in proximal direction and the needle has reached a predefined injection depth. The latch may likewise be arranged on the housing and the recess in the syringe carrier.

In another preferred embodiment at least one inwardly biased resilient snap may be arranged near the proximal end in the housing for preventing the needle sheath from translating in distal direction after having been translated into a proximal position for covering the needle. The needle can therefore not be re-exposed after injection.

The auto-injector may be configured to release the drive spring and plunger immediately when the needle sheath is pushed in distal direction. In this case the needle sheath and sheath linkage serve as the activating means.

Optionally, the needle sheath or the sheath linkage may be interlocked with the trigger button so as to require a sequence of operation wherein the needle sheath has to be translated into the auto-injector in distal direction from the initial position before the trigger button can be pressed. A sequence of operation further reduces the risk for inadvertent operation.

Optionally the syringe may be arranged for joint axial movement with a syringe holder slidably arranged in the housing. The syringe holder may be provided with at least two resilient syringe holder arms arranged distally, the syringe holder arms having a respective inclined surface for bearing against a shoulder in the plunger or a piston rod. The syringe holder arms may be supportable by an inner surface of the housing in order to prevent them from being flexed outward. Thus, when the drive spring is released the spring force forwarded by the piston rod of the plunger does not yet press against the stopper but against the syringe for forwarding it. Consequently, a so called wet injection is avoided, i.e. the liquid medicament is not leaking out of the hollow needle before the needle is inserted. A widened portion may be provided in the housing for allowing the syringe holder arms to flex outwards when the needle has reached its injection depth and the syringe holder has nearly reached a maximum proximal position thus allowing the shoulder in the piston rod to slip through the syringe holder arms and to switch load of the drive spring from the syringe to the stopper. This allows for defining the moment to start injecting the medicament.

The auto-injector may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
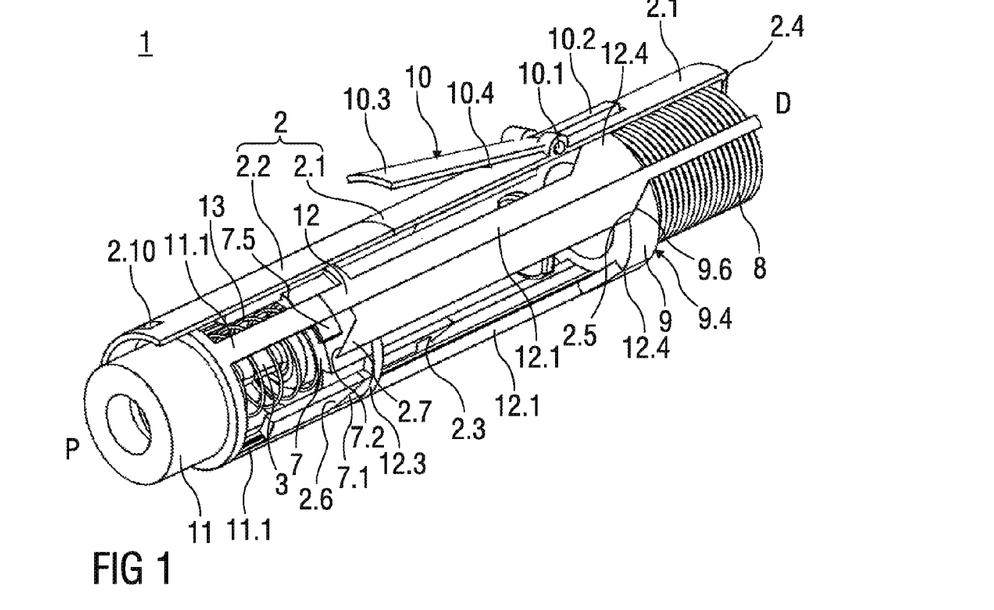
FIG. 1 is an isometric partial sectional view of an auto-injector in an initial state.
Figure 2:
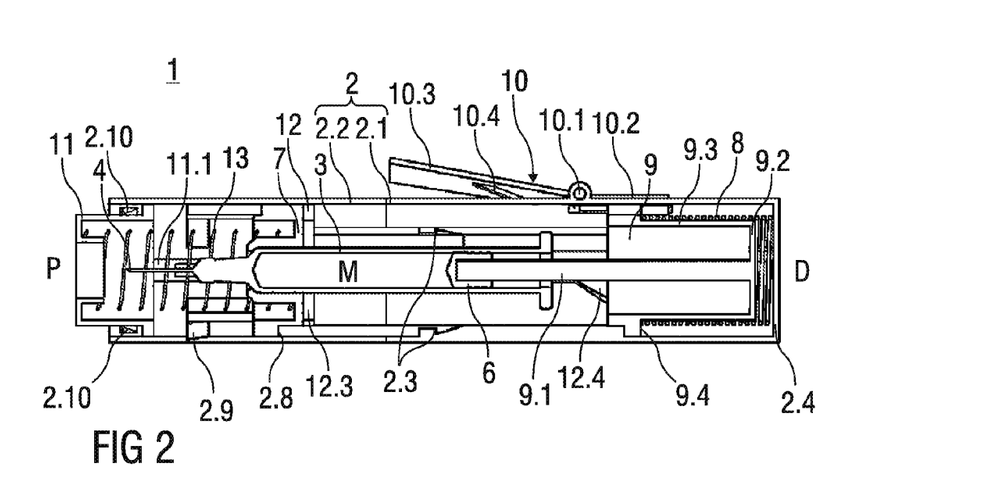
FIG. 2 is a longitudinal section of the auto-injector in the initial state.
Figure 3:
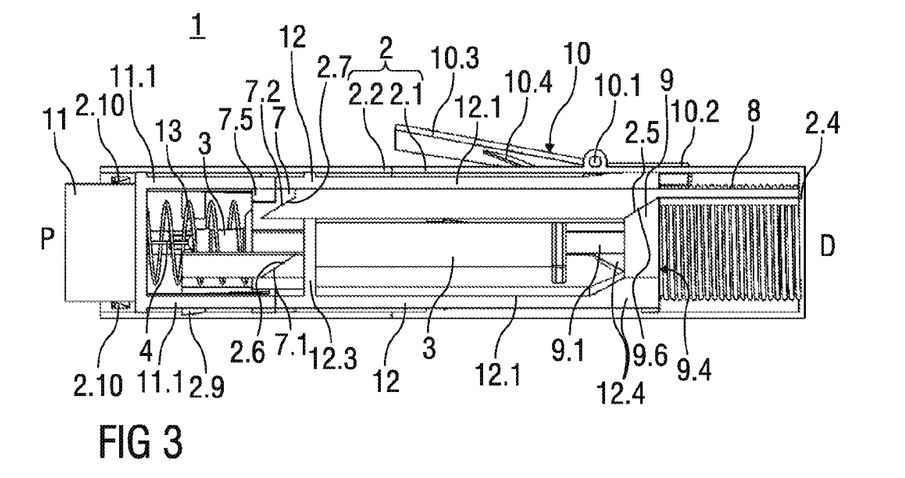
FIG. 3 is a longitudinal partial section of the auto-injector in the initial state, FIG. 4 are three detail views of the auto-injector.

FIGS. 1, 2 and 3 show an auto-injector 1 in an initial state or as delivered configuration. The auto-injector comprises an elongate housing 2 having a distal portion 2.1 and a proximal portion 2.2 telescoped into each other and connected by a snap fit 2.3. A syringe 3, e.g. a Hypak syringe, with a hollow needle 4 is arranged in the proximal portion 2.2 of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in the distal portion 2.1 of the auto-injector 1. A plunger 9 is arranged for forwarding the load of the drive spring 8 to the syringe 3 and/or to the stopper 6. A trigger button 10 is laterally arranged on the housing 2, the trigger button 10 having the shape of a rocker pivoted in a transversal axle 10.1 on the housing 2. In the initial state a distal arm 10.2 of the trigger button projects inwards through an aperture in the housing 2 in a manner to prevent the drive spring 8 from expanding. A proximal arm 10.3 of the trigger button 10 protrudes radially outward, preferably sprung by a resilient element 10.4. A needle sheath 11 having essentially the shape of a hollow cylinder is telescoped in a proximal end P of the housing 2 and protruding from the housing 2 in the initial state. Three sheath legs 11.1 extend from the needle sheath 11 in distal direction D. A sheath linkage 12 is arranged distally from the sheath legs 11.1 for interacting with the sheath legs 11.1 in a manner described below. The sheath linkage 12 comprises a number of linkage legs 12.1 extending in longitudinal direction. The plunger 9 comprises a piston rod 9.1 having an enlarged distal face 9.2 and a hollow plunger cylinder 9.3 attached to the distal face 9.2.

In the initial state the drive spring 8 in the shape of a compression spring is held compressed between a distal face 2.4 of the housing 2 and a collar 9.4 on the plunger 9.

The collar 9.4 is an incomplete collar with at least one circumferential gap 9.5 (cf. FIGS. 5, 7, 8, 10, 11, 13). An edge of the collar 9.4 towards one of the circumferential gaps 9.5 is shaped as a first ramp 9.6 arranged to interact with a corresponding second ramp 2.5 on the housing 2 in a manner to rotate the plunger 9 on translation from its initial distal position in proximal direction P. At least one of the linkage legs 12.1 has a distal wide end 12.4 arranged to fill one of the circumferential gaps 9.5 so as to prevent rotation and thus translation of the plunger 9 in the initial state. Furthermore, the distal arm 10.2 of the trigger button 10 is engaged in one of the circumferential gaps 9.5 in a manner to prevent rotation of the plunger 9 (not illustrated).

Figure 4A:
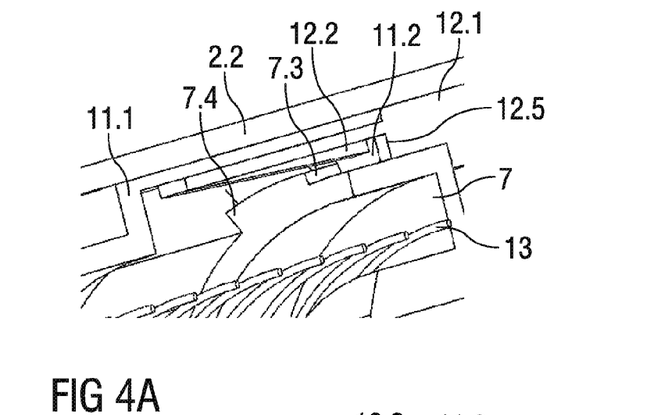
Figure 4B:
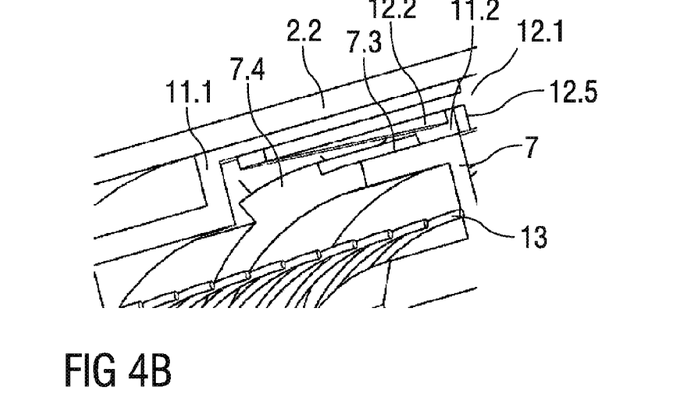
Figure 4C:
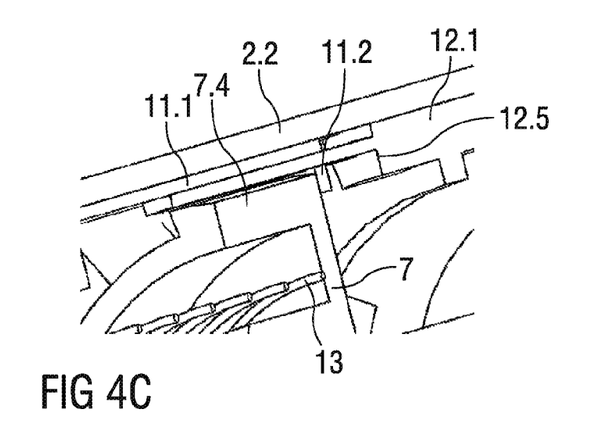
Figure 5:
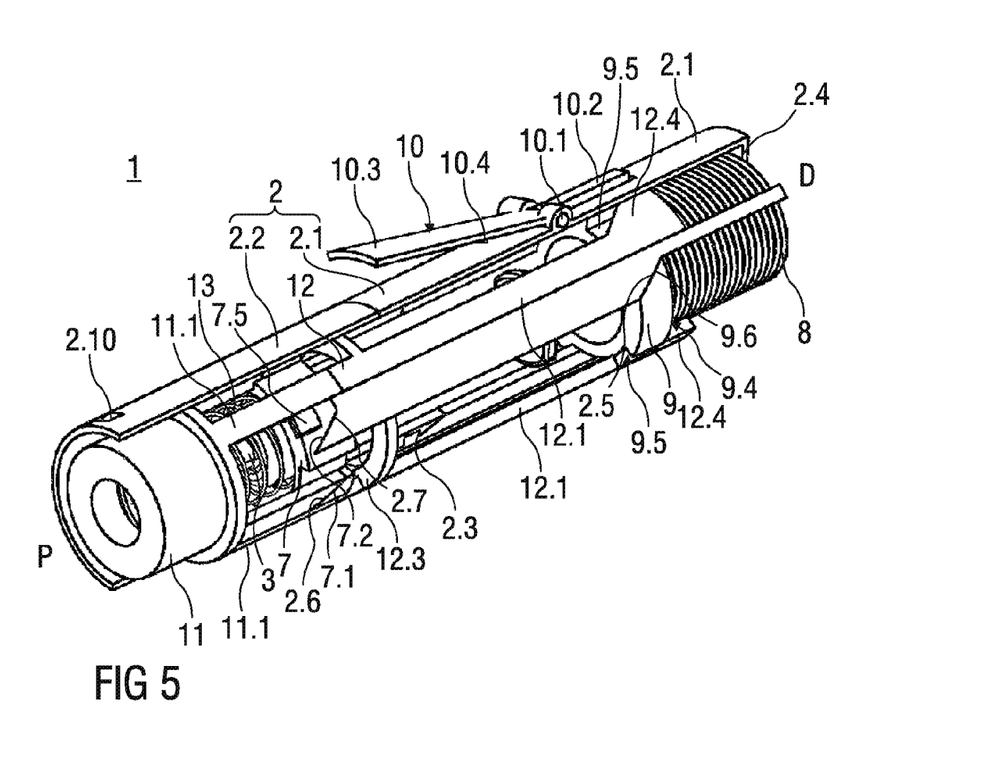
FIG. 5 is an isometric partial sectional view of the auto-injector with a needle sheath translated into the auto-injector.

The syringe carrier 7 has two circumferential third and fourth ramps 7.1, 7.2 engaged with two corresponding fifth and sixth ramps 2.6, 2.7 in the housing 2 so as to rotate the syringe carrier 7 on translation in proximal direction P. The sixth ramp 2.7 provides a backstop to prevent movement of the syringe carrier 7 in the distal direction D. In the initial state counter-clockwise rotation (seen from the distal end D) and hence translation in proximal direction P is prevented by a series of three splines created by the needle sheath 11 and sheath linkage 12. One of the splines is shown in FIGS. 4*a, b, c*). The other two splines are angularly spaced from the one in FIG. 4, preferably equally distributed over the circumference of the syringe carrier 7. Each spline consists of a distal end portion of one of the sheath legs 11.1 and a proximal end portion of one of the linkage legs 12.1. The sheath leg 11.1 exhibits a rib 11.2 protruding inwards from the distal end of the sheath leg 11.1, the rib 11.2 having an aperture for accommodating the proximal end portion of the linkage leg 12.1. The proximal end portion of the linkage leg 12.1 comprises a resilient tongue 12.2 connected to the linkage leg 12.1 near its proximal tip, extending in distal direction D and biased inwards so that it protrudes inwardly unless it is flexed into an aperture in the linkage leg 12.1. When the proximal end portion of the linkage leg 12.1 is held in the aperture of the rib 11.2 with a stop 12.5 on the linkage leg 12.1 abutting against the rib 11.2 of the sheath leg 11.1 as in FIGS. 4 *a* and *b* the inwardly protruding tongue 12.2 cannot return through the rib 11.2 and locks the sheath leg 11.1 to the linkage leg 12.1 for joint axial translation. In the initial position shown in FIG. 4*a* the rib 11.2 is engaged with a slot 7.3 in the syringe carrier 7 so as to prevent counter-clockwise rotation.

Translation of the syringe carrier 7 in distal direction D and clockwise rotation are prevented by the sixth ramp 2.7 on the proximal portion 2.2 (cf. FIG. 2).

In order to start an injection cycle the auto-injector 1 has to be pushed against an injection site, e.g. a patient's skin. Thus the needle sheath 11 is translated from a proximal position into the housing 2 in distal direction D. Furthermore, the trigger button 10 has to be pressed in order to release the drive spring 8.

Figure 6:
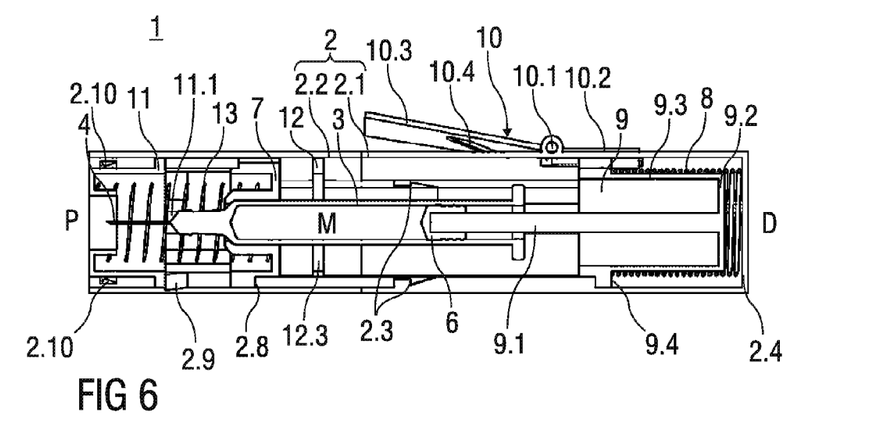
FIG. 6 is a longitudinal section of the auto-injector in the state as in FIG. 5.
Figure 7:
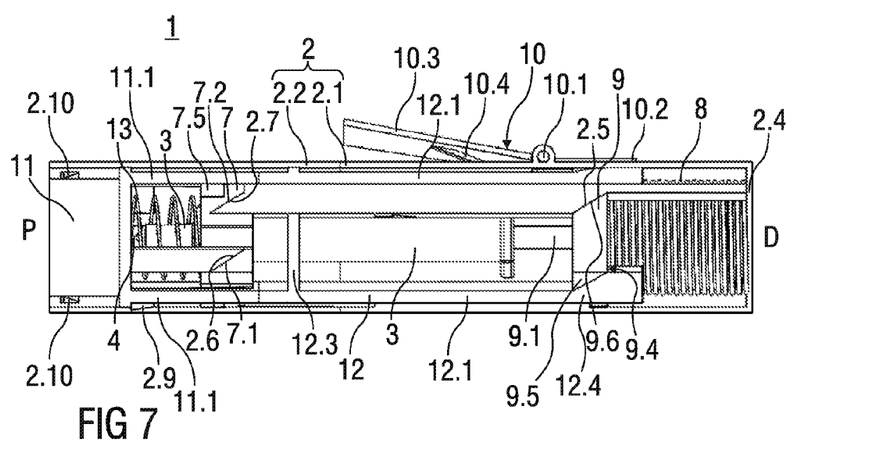
FIG. 7 is a longitudinal partial section of the auto-injector in the state as in FIG. 5.

The needle sheath 11 is biased in proximal direction P by a needle sheath spring 13 and prevented from moving too far forwards by a collar 12.3 of the sheath linkage 12 which references off a distal face of the syringe carrier 7. In the initial position the needle sheath 11 and the sheath linkage 12 are connected for joint axial motion (cf. FIGS. 4*a, b*) so the collar 12.3 of the sheath linkage 12 abutting against the distal face of the syringe carrier 7 keeps the needle sheath 11 from advancing. By placing the auto-injector 1 against the injection site and pushing the needle sheath 11 in distal direction D (see FIGS. 5, 6 and 7) the distal end of the spline which is thicker due to the rib 11.2 and due the distally adjacent part of the linkage leg 12.1 (cf. FIG. 4*a*) is moved in distal direction D relative to the slot 7.3 in the syringe carrier 7 and replaced by a thinner portion of the spline proximally from the rib 11.2 (cf. FIG. 4*b*). The spline is no longer engaged with the slot 7.3 so the syringe carrier 7 can now rotate about the third and fifth ramps 7.1, 2.6 on the inside of the proximal portion 2.2 and translate in proximal direction P if driven by the drive spring 8. The low force of the needle sheath spring 13 biasing the needle sheath 11 against the syringe carrier 7 holds the syringe 3 and syringe carrier 7 back until the drive spring 8 is released.

If the auto-injector 1 is removed from the injection site in this situation without pushing the trigger button 10, the needle sheath 11 and the sheath linkage 12 would return into their initial position as in FIGS. 1, 2 and 3. The ramp on the distal wide end 12.4 ensures that the sheath linkage 12 is guided back to its initial position. The thicker distal end of the spline would re-engage with the slot 7.3, returning the auto-injector 1 to its initial state.

With the needle sheath 11 pressed against the injection site and held in its distal position the syringe carrier 7 is free to rotate counter-clockwise and translate in proximal direction P. Furthermore, the distal wide end 12.4 of the linkage leg 12.1 is translated in distal direction D until an edge of the gap 9.5 is no longer engaged with the linkage leg 12.1 (cf. FIG. 7). Rotation of the plunger 9 is now only prevented by the distal arm 10.2 of the trigger button 10 engaged in the gap 9.5.

In order to trigger the auto-injector 1 the user must push the proximal arm 10.3 of the trigger button 10 inwards. The distal arm 10.2 projecting into the gap 9.5 in the plunger 9 is pulled out of the gap 9.5. The drive spring 8 pushes on the collar 9.4 of the plunger 9 thus translating the plunger 9 in proximal direction P and rotating it counter-clockwise due to the first ramp 9.6 of the plunger 9 sliding along the second ramp 2.5 on the housing 2. The piston rod 9.1 of the plunger 9 pushes on the stopper 6 of the syringe 3. As the force required to eject the liquid medicament M from the syringe is significantly higher than the force required to move the syringe 3 in proximal direction P, the syringe 3 translates in proximal direction P and the needle 4 is inserted into the injection site. As the syringe 3 translates the syringe carrier 7 translates with it and rotates counter-clockwise at the same time due to the engagement of the third and fifth ramps 7.1, 2.6.

As the syringe carrier 7 rotates, a cam 7.4 on the circumference of the syringe carrier 7 arranged clockwise from the slot 7.3 pushes the tongue 12.2 outwards into the aperture of the linkage leg 12.1 thus allowing the sheath leg 11.1 and the linkage leg 12.1 to separate and move independently.

The angles and widths of the ramps 9.6, 2.5, 2.6, 2.7, 7.1, 7.2 are matched so as to rotate the plunger 9, the syringe 3 and the syringe carrier 7 as a single body while the needle sheath 11 and the sheath linkage 12 do not rotate relative to the housing 2. This rotation completes before the needle 4 protrudes from the proximal end P of the housing 2. The remaining motion of the plunger 9, the syringe carrier 7, the syringe 3 and the needle 4 in proximal direction P until reaching an injection depth is a purely linear translation so the needle 4 does not screw into the injection site.

The injection depth is controlled by at least one resilient latch 7.5 on the circumference of the syringe carrier 7 flexing out into a recess 2.9 (cf. FIGS. 2, 3, 6, 7) in the housing 2 on translation of the syringe carrier 7 and abutting against a proximal edge of this recess 2.9. As the syringe carrier 7 translates the needle sheath spring 13 is compressed.

As the syringe 3 stops translating the piston rod 9.1 continues translating and pushes the stopper 6 in proximal direction P thus injecting the liquid medicament M through the hollow injection needle 4 into the injection site, i.e. into or through the patient's skin.

Figure 8:
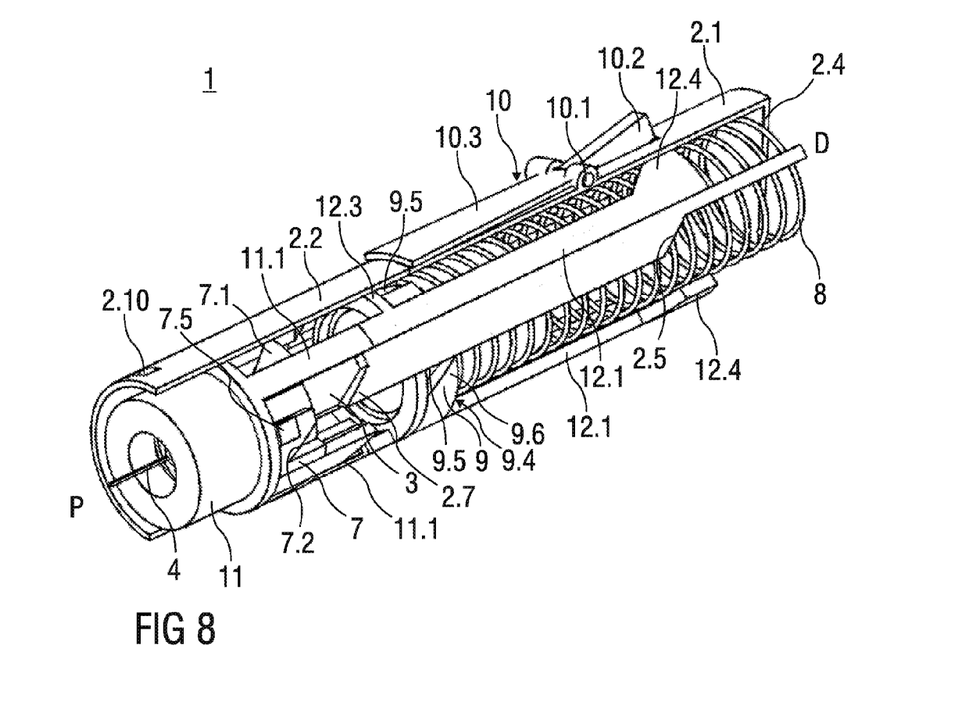
FIG. 8 is an isometric partial sectional view of the auto-injector with the needle inserted into an injection site at the end of an injection.
Figure 9:
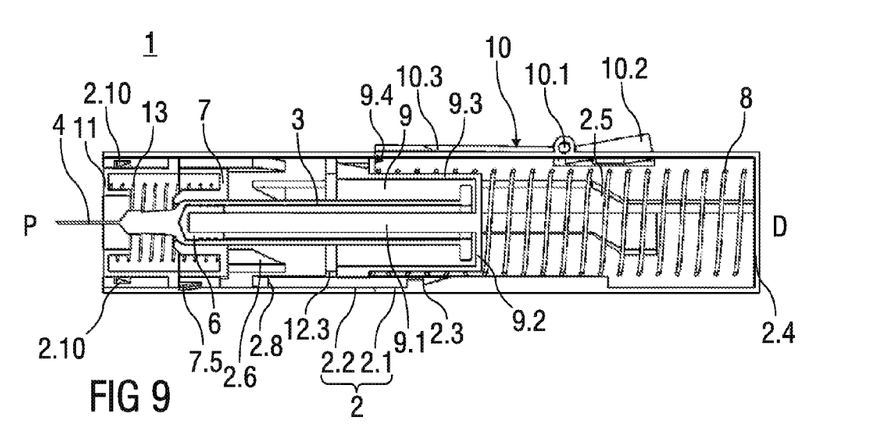
FIG. 9 is a longitudinal section of the auto-injector in the state as in FIG. 8.
Figure 10:
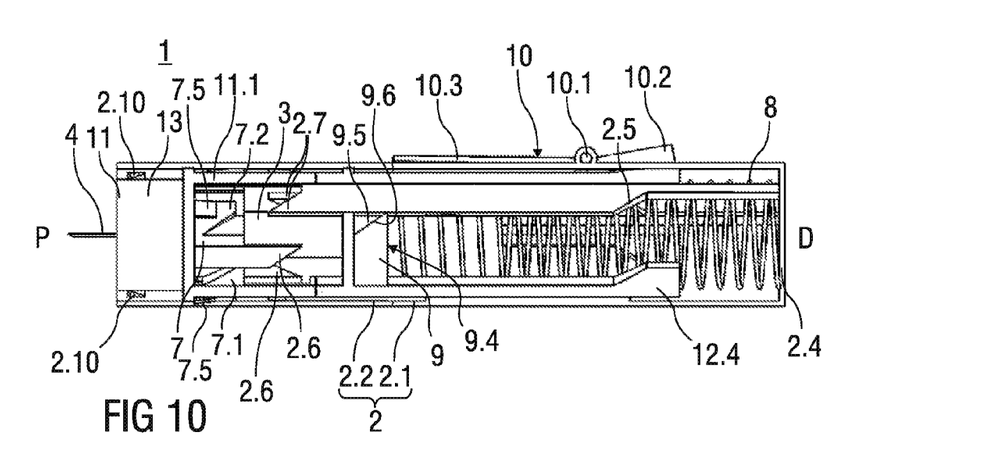
FIG. 10 is a longitudinal partial section of the auto-injector in the state as in FIG. 8.

FIGS. 8, 9 and 10 show the auto-injector 1 at the end of the injection. The stopper 6 has bottomed out in the syringe 3 and injected the entire contents of the syringe 3 into the injection site.

Figure 11:
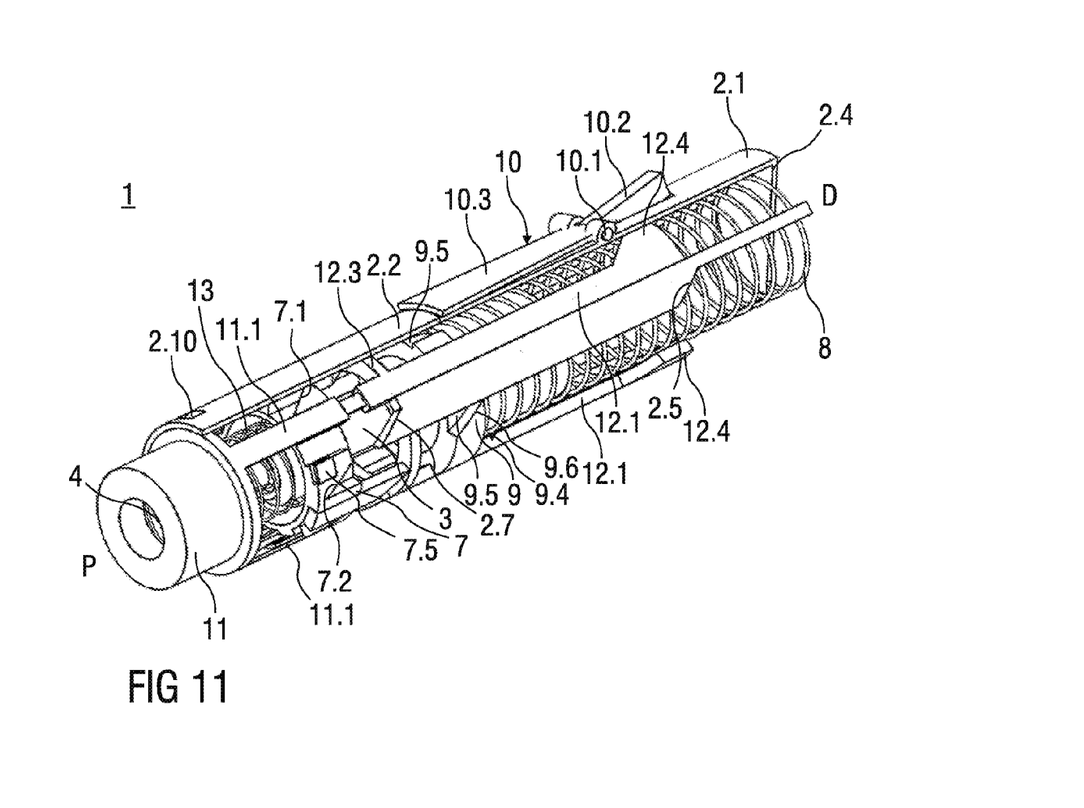
FIG. 11 is an isometric partial sectional view of the auto-injector with the needle sheath advanced after injection.
Figure 12:
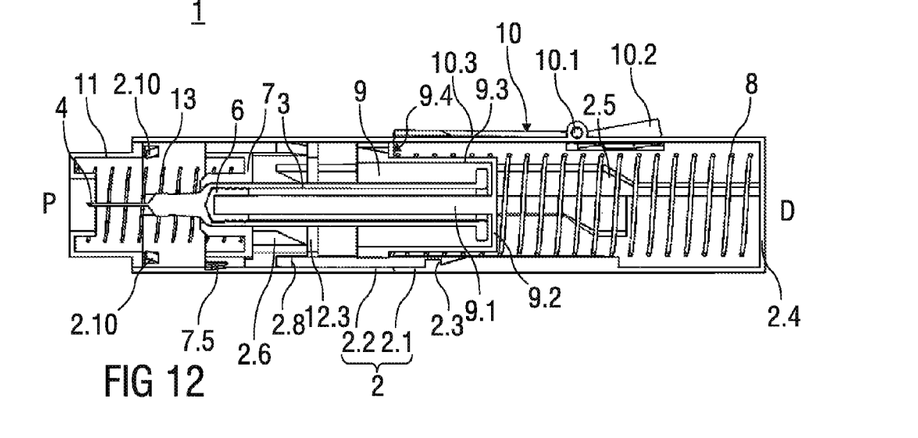
FIG. 12 is a longitudinal section of the auto-injector in the state as in FIG. 11.
Figure 13:
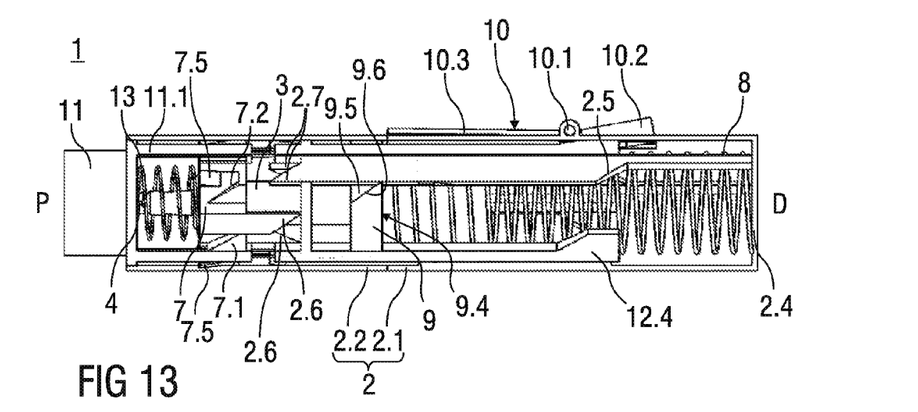
FIG. 13 is a longitudinal partial section of the auto-injector in the state as in FIG. 11.

When the auto-injector 1 is removed from the injection site during or at the end of injection the needle sheath 11 translates in proximal direction P due to the force of the needle sheath spring 13 into a proximal position (see FIGS. 11, 12 and 13). Since the sheath leg 11.1 and the linkage leg 12.1 have been separated by the cam 7.4 disengaging the tongue 12.2, translation of the needle sheath 11 in proximal direction P is no longer restricted by the sheath linkage 12. Instead the needle sheath 11 is translated into a position where it protrudes even more from the housing 2 than in the initial state until the rib 11.2 of the sheath leg 11.1 abuts against the distal face of the syringe carrier 7 as in FIG. 4c.

Figure 14:
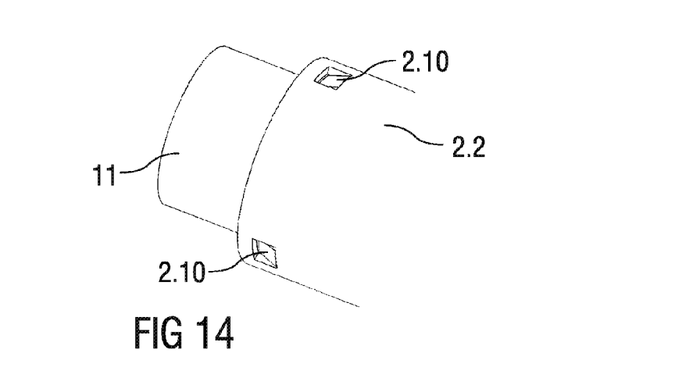
FIG. 14 is a detail of a proximal end of the auto-injector with the needle sheath advanced and snapped to the housing 2.

When the needle sheath 11 is translated far enough in proximal direction P to protect the user from the needle 4, inwardly biased resilient snaps 2.10 in the proximal portion 2.2 are pushed out by the translating needle sheath 11 and then move inwards permanently preventing the needle sheath 11 from moving back into the housing 2 in distal direction D (see details in FIG. 14).

In the illustrated embodiment the trigger button 10 may be pressed before or after translation of the needle sheath 11 in distal direction D in the initial state or even at the same time. Optionally, the sheath linkage 12 may be interlocked with the trigger button 10 so as to require a sequence of operation wherein the needle sheath 11 has to be translated into the auto-injector 1 before the trigger button 10 can be pressed.

The counter-clockwise sense of rotation of the plunger 9 and the syringe carrier 7 have been arbitrarily chosen in the above embodiment. In an alternative embodiment the plunger 9 and/or the syringe carrier 7 may be arranged to rotate clockwise due to a different arrangement of the ramps 9.6, 2.5, 2.6, 2.7, 7.1, 7.2.

Instead of the pairs of ramps 9.6 and 2.5, 7.1 and 2.6, 7.2 and 2.7 it would be sufficient to provide a ramp on just one of the involved components engaged with a follower on the respective other component.

The auto-injector 1 of the above embodiment exhibits three sheath legs 11.1 and linkage legs 12.1. Likewise, another number could be chosen.

In an alternative embodiment the auto-injector 1 may be arranged to rotate the plunger 9, the syringe carrier 7, the syringe 3 and the needle 4 until reaching the injection depth even during needle insertion.

The rib 11.2 may be likewise arranged on the linkage leg 12.1 with the distal portion of the sheath leg 11.1 extending through the aperture in the rib and the tongue being part of the sheath leg 11.1.

FIGS. 5 to 10 show the needle sheath 11 flush with the proximal end P of the housing 2 for triggering an injection. It is likewise possible to disengage the spline from the slot 7.3 and the distal wide end 12.4 from the gap 9.5 when the needle sheath 11 is still slightly protruding from the housing 2.

Optionally the syringe 3 may be arranged for joint axial movement with a syringe holder slidably arranged in the housing 2. The syringe holder may be provided with at least two resilient syringe holder arms arranged distally, the syringe holder arms having a respective inclined surface for bearing against a shoulder in the piston rod 9.1. The syringe holder arms may be supportable by an inner surface of the housing 2 in order to prevent them from being flexed outward.

Thus, when the drive spring 8 is released the spring force forwarded by the piston rod 9.1 of the plunger 9 does not yet press against the stopper 6 but against the syringe 3 for forwarding it. Consequently, a so called wet injection is avoided, i.e. the liquid medicament M is not leaking out of the hollow needle 4 before the needle 4 is inserted. A widened portion may be provided in the housing 2 for allowing the syringe holder arms to flex outwards when the syringe holder has nearly reached a maximum proximal position thus allowing the shoulder in the piston rod 9.1 to slip through the syringe holder arms and to switch load of the drive spring 8 from the syringe 3 to the stopper 6. This allows for defining the moment to start injecting the medicament M.

The invention claimed is:

1. Auto-injector for administering a dose of a liquid medicament (M), the auto-injector having a distal end (P) and a proximal end (D) with an orifice intended to be applied against an injection site and comprising:
    an elongate housing arranged to contain a syringe with a hollow needle and a stopper for sealing the syringe and displacing the medicament (M), wherein the syringe is slidably arranged with respect to the housing,
    a driver capable of, upon activation:
       pushing the needle from a retracted position into an advanced position through the orifice and past the proximal end (P), and
       operating the syringe to supply the dose of medicament (M),
    a plunger for transmitting power from the driver to at least one of the syringe or the stopper,
    an activator arranged to lock the driver in a compressed state prior to manual operation and capable of, upon manual operation, releasing the driver for injection,
    wherein translation of the needle and the syringe or translation of the plunger in a longitudinal direction is controlled by at least one ramp or one thread so as to cause the syringe or the plunger to rotate, during administering the dose of the liquid medicament, about a longitudinal axis of the auto-injector when translated at least during part of the translation.

2. Auto-injector according to claim 1, wherein the plunger is arranged to be rotated by at least one ramp on translation from an initial distal position in proximal direction (P), wherein the activator comprises a trigger button arranged to be engaged with the plunger so as to prevent rotation and thus translation of the plunger prior to operation, wherein the trigger button is arranged to be disengaged from the plunger when operated.

3. Auto-injector according to claim 1, wherein the plunger is arranged to be rotated by at least one ramp on translation from an initial distal position in proximal direction (P), wherein a needle sheath having essentially the shape of a hollow cylinder is arranged to surround the needle, the needle sheath slidable in the longitudinal direction with respect to the syringe and biased in proximal direction (P), wherein in the initial state the needle sheath is in its initial position protruding beyond a proximal end of the housing, wherein the needle sheath is arranged to directly or indirectly engage the plunger in a manner to prevent rotation and thus translation of the plunger in the initial state and wherein the plunger is disengaged from the needle sheath upon translation of the needle sheath in distal direction (D) from the initial position.

4. Auto-injector according to claim 3, wherein a sheath linkage with at least one linkage leg, slidable in the longitudinal direction, and a syringe carrier for holding the syringe are provided, the syringe and syringe carrier arranged for joint axial translation and rotation relative to the needle sheath, wherein the sheath linkage comprises a restrictor configured to translate in proximal direction (P) with respect to the syringe by abutting against the syringe carrier, wherein in the initial state the sheath linkage is abutted against the syringe carrier and latched to the needle sheath for joint axial translation, wherein the syringe carrier exhibits at least one cam on its circumference, wherein the cam is arranged to de-latch the needle sheath from the sheath linkage on rotation of the syringe carrier so as to release the needle sheath for being translated in proximal direction (P) and cover the needle, wherein a distal wide end of the of the linkage leg is arranged to engage the plunger in a manner to prevent rotation and thus translation of the plunger in the initial state, wherein the wide end is arranged to disengage from the plunger on translation of the needle sheath and sheath linkage in distal direction (D) from the initial position.

5. Auto-injector according to claim 4, wherein the syringe carrier exhibits at least one slot on its circumference and that the latched needle sheath and sheath linkage form at least one spline, each spline arranged for engaging one of the slots in the initial position so as to prevent rotation of the syringe carrier, wherein the spline is arranged to be disengaged from the slot on translation of the needle sheath in distal direction (D) from the initial position.

6. Auto-injector according to claim 4, wherein the syringe carrier is arranged to be rotated by at least one ramp on translation from an initial distal position in proximal direction (P) so as to de-latch the needle sheath from the sheath linkage.

7. Auto-injector according to claim 4, wherein the needle sheath comprises at least one sheath leg extending from the needle sheath in distal direction (D), wherein the spline consists of a distal end portion of the sheath leg and a proximal end portion of the linkage leg, wherein a rib protrudes inwards from the distal end of the sheath leg, the rib having an aperture for accommodating the proximal end of the linkage leg, wherein the proximal end portion of the linkage leg comprises an inwardly biased resilient tongue connected to the linkage leg at one end and with the other free end engaged proximally behind the rib in the initial position so as to prevent removal of the proximal end portion of the linkage leg through the aperture in the rib, wherein the tongue is arranged to be flexed outwards by the cam on rotation of the syringe carrier so as to align it with the linkage leg and allow the linkage leg to be at least partially pulled out of the aperture in the rib.

8. Auto-injector according to claim 1, wherein the driver is a compression spring distally grounded in the housing and proximally pushing on the plunger.

9. Auto-injector according to claim 4, wherein the angles and widths of the ramps are matched so as to rotate the plunger, the syringe and the syringe carrier as a single body.

10. Auto-injector according to claim 1, wherein rotation of the syringe by the ramps stops before the needle protrudes from the proximal end (P) of the housing or from the needle sheath.

11. Auto-injector (1) according to claim 1, wherein rotation of the syringe by the ramps continues until the needle has reached its injection depth.

12. Auto-injector according to claim 1, wherein at least one resilient latch is arranged on the circumference of the syringe carrier for flexing outwards into a respective recess in the housing when the syringe carrier, syringe and needle have been translated in proximal direction (P) and the needle has reached a predefined injection depth.

13. Auto-injector according to claim 3, wherein at least one inwardly biased resilient snap is arranged near the proximal end (P) in the housing for preventing the needle sheath from translating in distal direction (D) after having been translated into a proximal position for covering the needle.

14. Auto-injector according to claim 4, wherein the needle sheath or the sheath linkage is interlocked with the trigger button in such a manner that the trigger button can be operated only if the needle sheath has been translated from its initial position in distal direction (D).

15. Auto-injector according to claim 1, wherein the syringe is arranged for joint axial movement with a syringe holder which is slidably arranged in the housing, wherein the syringe holder is provided with at least one resilient syringe holder arm arranged distally, the syringe holder arm having a respective inclined surface for bearing against a shoulder on the plunger, wherein the syringe holder arm is supportable by an inner surface of the housing in order to prevent it from being flexed outward and wherein a widened portion is provided in the housing for allowing the syringe holder arm to flex outwards when the syringe holder has nearly reached a maximum proximal position thus allowing the shoulder of the plunger to slip past the syringe holder arm and to switch load of the drive spring from the syringe to the stopper.

* * * * *